United States Patent [19]

Kaufman

[11] 4,254,415

[45] Mar. 3, 1981

[54] SYSTEM FOR REVEALING CRACKS IN CYLINDRICAL MEMBERS SUCH AS BOLTS, AXLES, ETC., IN SITU

[76] Inventor: Mark Kaufman, 5725 Leger, Cote St. Luc, Quebec, Canada, H4W 2E5

[21] Appl. No.: 133,304

[22] Filed: Mar. 24, 1980

[51] Int. Cl.³ ............................................. C08B 21/00
[52] U.S. Cl. ........................................ 340/679; 73/37; 116/70; 340/626
[58] Field of Search ........................ 340/679, 626, 540; 73/37, 46, 49.8, 40; 116/70, 67 R, 208

[56] References Cited

U.S. PATENT DOCUMENTS

| | | | |
|---|---|---|---|
| 1,488,982 | 4/1924 | Goyne | 116/70 |
| 4,145,915 | 3/1979 | Oertle et al. | 73/37 |
| 4,201,974 | 5/1980 | Fima | 116/208 |

Primary Examiner—Glen R. Swann, III
Attorney, Agent, or Firm—Melvin Sher; Alan Swabey; Robert Mitchell

[57] ABSTRACT

An elongated cylindrical member, such as an axle, a bolt, stud, rivet, supporting column, etc., has means for the in situ detection and indication of cracks therein. The member is generally solid and includes, in accordance with the invention, a cavity extending inwardly from at least one end of the member and terminating in a bottom surface of the cavity. A plurality of holes extend inwardly from the bottom surface of the cavity and are disposed in circular arrangement around the bottom surface of the cavity and adjacent to the periphery of the member. A ring member is disposed in the cavity, the bottom surface of the ring member being spaced from the bottom surface of the cavity to define a chamber therebetween. An opening extends through the ring member from the top surface to the bottom surface thereof, and valve means are inserted in the opening to permit the insertion of gas under pressure into the chamber and into the holes. When a crack develops in the member and crosses one of the holes, the gas under pressure will escape through the crack from the chamber. The member includes a detector for determining that the gas has escaped from the chamber and holes to thereby detect the crack.

7 Claims, 2 Drawing Figures

SYSTEM FOR REVEALING CRACKS IN CYLINDRICAL MEMBERS SUCH AS BOLTS, AXLES, ETC., IN SITU

BACKGROUND OF INVENTION

1. Field of the Invention

The invention relates to an elongated cylindrical member, such as an axle, bolt, or the like, having means for the in situ detection and indication of cracks therein.

2. Description of Prior Art

Cracks in axles and bolts have contributed to severe accidents in railway cars, airplanes, and other moving vehicles. These cracks are often hairline cracks which cannot be easily visually detected. Yet quite often, the bolts and axles are only visually inspected. Of course, means do exist for the mechanical and/or electronic inspection of axles and bolts and the like, but they are relatively cumbersome and can be used under only special conditions. Thus, such mechanisms cannot be used when the vehicles are in motion.

The prior art also teaches various strain indicators for bolts as exemplified in U.S. Pat. No. 2,562,831, issued July 31, 1951 to A. R. Stone; U.S. Pat. No. 3,772,759, issued Nov. 20, 1973 to T. W. Bunyan; U.S. Pat. No. 3,799,108, issued Mar. 26, 1974 to J. E. Mosow; U.S. Pat. No. 3,841,193, issued Oct. 15, 1974 to A. Ito; U.S. Pat. No. 4,002,139, issued Jan. 11, 1977 to W. J. Payne; and U.S. Pat. No. 4,041,776, issued Aug. 16, 1977 to W. J. Payne. However, such strain indicators detect only the tightening strain applied to the bolts; they do not detect the presence or absence of cracks in the bolts. In addition, these machines can be used only under static conditions.

All of the above-mentioned mechanisms are further characterised by the fact that they exist separately of the bolts, axles, etc., and do not constitute a part of the bolts, axles, etc., themselves.

SUMMARY OF INVENTION

It is therefore an object of the invention to provide an elongated cylindrical member, such as an axle, bolt, or the like, having means for detecting and indicating the presence of cracks therein.

In accordance with the invention, an elongated cylindrical member, such as an axle, bolt, or the like, having means for the in situ detection and indication of cracks therein, said member being generally solid, comprises: a cavity extending inwardly from at least one end of said member, and terminating in a bottom surface of said cavity; a plurality of holes extending inwardly from said bottom surface of said cavity and disposed in circular arrangement around said bottom surface of said cavity and adjacent the periphery of said member; a ring member disposed in said cavity, said ring member having a top surface and a bottom surface, the bottom surface of said ring member being spaced from the bottom surface of said cavity to define a chamber therebetween; an opening extending through said ring member from the top surface to the bottom surface thereof; valve means in said opening for inserting gas under pressure into said chamber and said holes; wherein, when a crack develops in said member and crosses one of said holes, said gas under pressure will escape, via said crack, from said chamber and said holes; and means for detecting that said gas has escaped from said chamber and said holes to thereby detect said crack.

The ring may comprise an insert member which is in airtight engagement with the walls of said cavity and which is force fitted into said cavity.

The valve means may comprise a slidable means in said opening in said ring member and spring means biasing said slidable means inwardly.

Cap means may be provided for covering said valve means, said cap means having electrical contact means disposed thereon.

A further electrical contact means can be disposed on the bottom surface of said cavity, said contact means on said cap means being engageable with said further electrical contact means when said gas has escaped from said holes.

Indicator means are connected to said further contact means, whereby, when said contact means on said cap means engages said further electrical contact means, said indicator means is activated to indicate the presence of a crack in said member.

Preferably, said gas under pressure is air.

BRIEF DESCRIPTION OF DRAWINGS

The invention will be better understood by an examination of the following disclosure together with the accompanying drawings in which.

DESCRIPTION OF PREFERRED EMBODIMENTS

Figure 1:
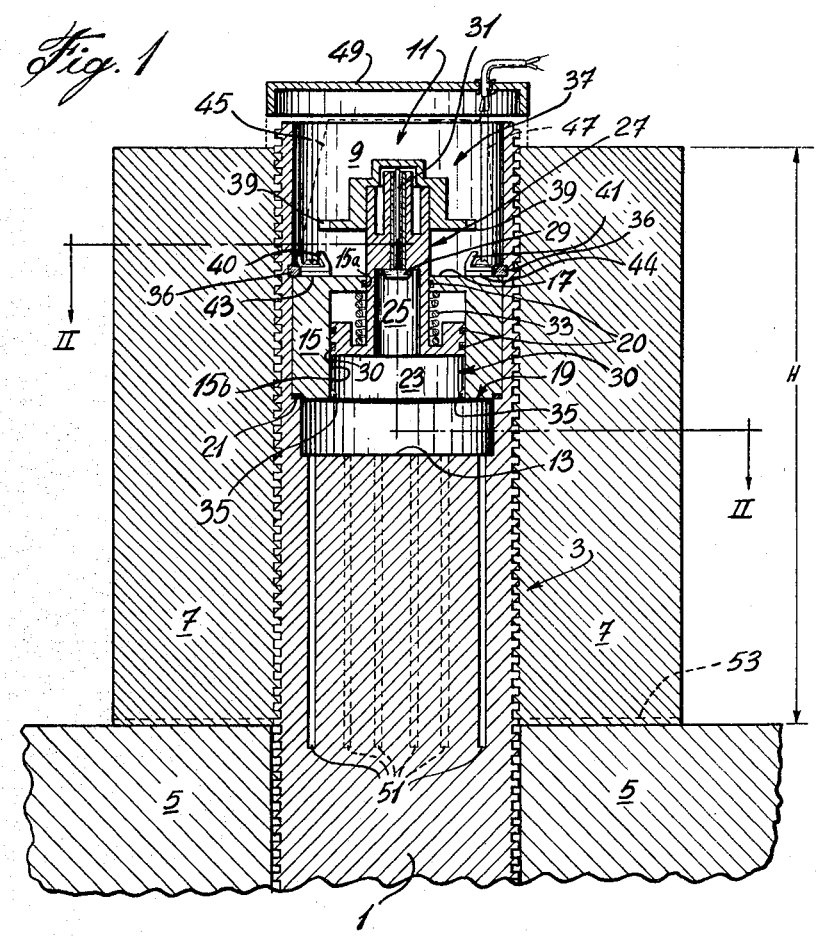
FIG. 1 is a section in an elevational view.

The invention as illustrated herein is embodied in a bolt. However, as will be apparent, the invention can also be embodied in any other elongated cylindrical member wherein the detection of cracks is critical. For example, the invention can also be embodied in an axle of a moving vehicle such as an axle of a car or an axle of a railway car, studs, rivets, supporting columns, etc.

Referring to the drawings, the bolt, illustrated generally at 1, includes a threaded outer surface 3 as usual. The bolt is disposed in a housing 5, and a nut 7 is mounted on the upper portion of the bolt.

A cavity 9 extends inwardly from one end 11 of the bolt and terminates in a bottom surface 13 of the cavity. Disposed in the cavity is a ring member 15 having a top surface 17 and bottom surface 19. The bottom surface 19 of the ring member is spaced from the bottom surface 13 of the cavity by means of an annular support member 21 to define, between the bottom surfaces a chamber 23. Opening 25 extends through the ring member from the top surface to the bottom surface thereof.

A valve means 27 is disposed in the opening 25. The valve means includes a sliding member 29 and stem portion 31. The sliding member is biased inwardly by spring 33, but is prevented from moving below the bottom surface of the ring by burred edge 35 of the bottom surface of the ring. As is apparent, means other than 35 could be used to prevent this descent of 29. The ring member is prevented from moving upwardly of the cavity by locking ring 36.

Cap 37, having a conduction ring 39 at one end thereof, is disposed to be mounted over the top end of the valve as will be explained below. The cap member 37 may be made of an insulating material such as a plastic material.

Disposed on the top surface 17 of the ring 15 are contact members 40 and 41 made of a conductive material. The contact members are insulated from the ring member 15 by insulator pads 43 and 44. As will be appreciated, these insulator pads will be needed only if the ring 15 is made of a conductive material. If the ring 15 is made of an insulating material, then the insulator pads 43 and 44 are not required.

Leads 45 and 47 are electrically connected to contact members 40 and 41 respectively, and these leads are connected to an indicator device which is not shown in the drawings.

Cover plate 49 is adapted to fit over the nut and bolt arrangement to prevent dust, etc. from entering into the cavity 9.

Figure 2:
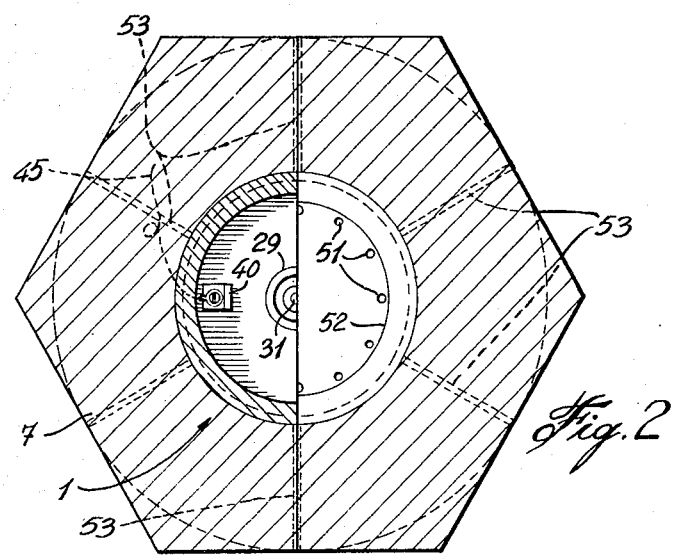
FIG. 2 is a section along line II—II of FIG. 1.

A plurality of holes 51 extend inwardly from the bottom surface 13 of the cavity. As can be seen in FIG. 2, the holes are disposed in circular arrangement around the bottom surface and adjacent the periphery of the bolt.

In operation, the invention works as follows:

Preferably, the ring and valve and spring arrangements are prefabricated as a single unit, and the unit is force fit into the cavity 9 until the bottom surface of the ring makes contact with the top of the annular support 21. A force fit is necessary to ensure that the wall of the ring member is in airtight engagement with the wall of the cavity. To help in this, it may be useful to have rubber O-rings or washers 20 in the wall of the ring member or in the wall of the cavity.

After the ring member is inserted in the cavity, the locking ring 36 is mounted as is well known in the art.

Gas under pressure, and having 0% humidity, is then inserted, through the valve 27, into the chamber 23 and the holes 51. Preferably, the gas is air. In this regard, the valve shown in the drawing is similar to a valve on an automobile tire so that a hose similar to an automobile air hose could be used to insert the air in this embodiment. However, as the gas or air must have 0% humidity, it obviously could not be an actual automobile air hose. As is well known, other valve means could be used whereupon other sources of air under pressure would be used to fill the interior of the bolt.

When the holes 51 and the chamber 23 are completely full, the air under pressure will force the sliding member 29 outwardly so that, when the cap 37 is disposed on top of the valve, the ring 39 will not be in contact with the contacts 40 and 41. As will be appreciated, the walls 30 of the valve must be in airtight engagement with the portions 15a and 15b of the ring 15.

After the chamber and holes have been filled with air under pressure, the cover plate 49 is disposed over the nut to keep dust out of the interior of the bolt.

As is well known, cracks developing in bolts, or other elongated cylindrical members of a like nature, will develop close to the periphery of the member. Thus, eventually any crack which develops will pass through one of the holes 51 as shown at 52 in FIG. 2. When this transpires, there will be communication between that particular hole 51 and the exterior of the elongated member. Thus, air from hole 51 will be able to escape out of the interior of the elongated member.

Because chamber 23 permits communication between the holes 51, eventually air from chamber 23 will also escape out of the crack, and air from the other holes will be drawn into chamber 23 and then into the particular hole 51 adjacent the crack, so that air will keep escaping from the interior of the elongated member until such time the pressure inside the bolt is equal to the ambient pressure of the environment in which the bolt is disposed at the time. To permit easier escape of the air, it is preferably arranged that the threads of a nut and bolt are not in airtight engagement with each other.

To aid the escape of air even more, a plurality of grooves or channels 53 may be provided around the periphery of the nut or any other member which may surround the outward end of any other elongated cylindrical member on which the invention is used.

When the pressure inside of the bolt has equalized with the ambient pressure, the spring 33 will force the member 29 inwardly so that the conductive ring 39 will make contact with the contacts 40 and 41. In this regard, the force of the spring 33 will be adjusted so that 39 is in positive physical and electrical contact with the contact members 40 and 41 when member 29 is forced downwardly.

Contacts 40, 41 and the conductive ring 39 act as a "switch" to turn an indicator device as well known in the art. The indicator device could be a light, and/or a buzzer, in a maintenance panel e.g., in the cockpit of the aircraft. In any case, the turning on of the indicator will indicate that a crack has developed in the bolt.

It will be appreciated that even the most minute of cracks will cause the same action, i.e., the expulsion of air under pressure, from the interior of the bolt. Thus, cracks can be detected and indicated long before they become serious problems.

Although the holes 51 could weaken the bolt slightly, this can be easily compensated for by slightly increasing the diameter of the bolt. It is anticipated that the size of the holes would be approximately 1/32 of an inch in diameter and spaced so that their centers are one inch apart. It is also possible that the holes extend almost to the bottom of a bolt.

When the invention is used on a bolt going into a blind hole, the head of the bolt should be strengthened by providing a truncated cone extension from the bottom of the head of the bolt and extending and tapering towards the bolt.

Concerning the height H of the nut, as is well known, generally speaking, a nut for fastening the bolt should be of a height equal to the diameter of the bolt. This is to provide sufficient holding power for the nut and bolt arrangement. In this particular case, it will extend to within ½" of the top of free end, 11, of the bolt. This is to provide protection for the hollowed out portion of the bolt extending outside of the housing 5, while still leaving a free end of the bolt on which cap 49 can be mounted.

Although the foregoing has described electronic monitoring, it will be appreciated that visual monitoring of the actual system is also possible. Thus, with cover plate 49 being made transparent, the system can be visually monitored by seeing if cap member 37 is in its "up" or "down" position. This would be especially useful on, for example, train axles. Also, cover plate 49 could be made easily removable and the system could be tested by pressing on cap member 37. If cap member 37 can be easily pushed down, some air has escaped. If it resists pushing, there are no cracks.

Although only a single embodiment has been described, this was for the purpose of illustrating, but not limiting, the invention. Various modifications, which will come readily to the mind of one skilled in the art, are within the scope of the invention as defined in the appended claims.

I claim:

1. An elongated cylindrical member, such as an axle, bolt, or the like, having means for the in situ detection and indication of cracks therein, said member being generally solid, and comprising:
  a cavity extending inwardly from at least one end of said member, and terminating in a bottom surface of said cavity;
  a plurality of holes extending inwardly from said bottom surface of said cavity and disposed in circular arrangement around said bottom surface of said cavity and adjacent the periphery of said member;
  a ring member disposed in said cavity, said ring member having a top surface and a bottom surface, the bottom surface of said ring member being spaced from the bottom surface of said cavity to define a chamber therebetween;
  an opening extending through said ring member from the top surface to the bottom surface thereof;
  valve means in said opening for inserting gas under pressure into said chamber and said holes;
  wherein, when a crack develops in said member and crosses one of said holes, said gas under pressure will escape, via said crack, from said chamber and said holes; and
  means for detecting that said gas has escaped from said chamber and said holes to thereby detect said crack.

2. A member as defined in claim 1 wherein said ring comprises an insert member which is in airtight engagement with the walls of said cavity and which is force fitted into said cavity.

3. A member as defined in claim 2 wherein said valve means comprises a slidable means in said opening in said ring member, and spring means biasing said slidable means inwardly.

4. A member as defined in claim 3 and further comprising cap means for covering said valve means, said cap means having electrical contact means disposed thereon.

5. A member as defined in claim 4 and further including further electrical contact means disposed on the bottom surface of said cavity;

said contact means on said cap means being engageable with said further electrical contact means when said gas has escaped from said chamber and said holes.

6. A member as defined in claim 5 and comprising indicator means connected to said further contact means;

whereby, when said contact means on said cap means engages said further electrical contact means, said indicator means is activated to indicate the presence of a crack in said member.

7. A member as defined in any of claims 1 to 6 wherein said gas is air having 0% humidity.

* * * * *